United States Patent

Bourgogne et al.

Patent Number: 4,739,101
Date of Patent: Apr. 19, 1988

[54] METHOD FOR THE PREPARATION OF FIBRATES

[75] Inventors: Jean-Pierre Bourgogne, Longvic; Roland Sornay, Ruffey les Echirey, both of France

[73] Assignee: Fournier Innovation et Synergie, Paris, France

[21] Appl. No.: 43,184

[22] Filed: Apr. 27, 1987

[30] Foreign Application Priority Data

Apr. 30, 1986 [FR] France ................. 86 06258

[51] Int. Cl.$^4$ ............................................. C07C 69/76
[52] U.S. Cl. ............................... 560/61; 560/62; 560/45
[58] Field of Search ........................... 560/61, 62, 45

[56] References Cited

U.S. PATENT DOCUMENTS

| 3,759,950 | 9/1973 | Grant | 560/61 |
| 3,795,691 | 3/1974 | Douglas | 560/61 |

FOREIGN PATENT DOCUMENTS

| EP82413 | 6/1983 | European Pat. Off. | 560/61 |
| EP128658 | 12/1984 | European Pat. Off. | 560/61 |
| 2060573 | 6/1971 | Fed. Rep. of Germany | 560/61 |

Primary Examiner—Paul J. Killos
Attorney, Agent, or Firm—Max Fogiel

[57] ABSTRACT

The present invention relates to a method for the preparation of fibrates of the formula I according to the mechanism:

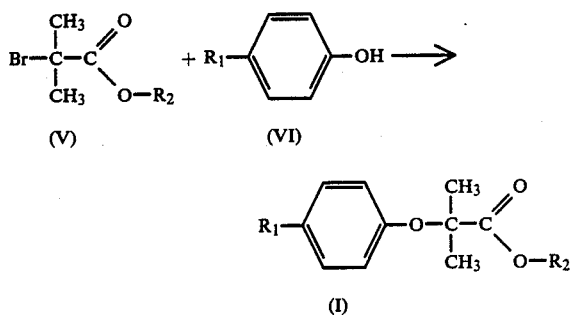

in which $R_1$ represents especially a halogen atom (in particular F, Cl or Br, the preferred halogen atom being Cl) or an acetyl, (4-chlorophenyl)hydroxymethyl, 4-chlorobenzoyl or 2-(4-chlorobenzamido)ethyl group and $R_2$ represents a $C_1$–$C_4$ alkyl group in which the hydrocarbon chain is linear or branched, the reaction V+VI being carried out without a solvent.

9 Claims, No Drawings

METHOD FOR THE PREPARATION OF FIBRATES

The present invention relates to a novel method for the preparation of fibrates.

The term "fibrates" denotes a family of compounds which have hypocholesterolemic and hypolipidemic properties and correspond to the general formula:

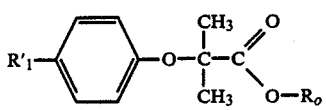   (I$_o$)

in which R'$_1$ represents especially a halogen atom or a 2,2-dichlorocyclopropyl group, a (4-chlorophenyl)hydroxymethyl group, a 4-chlorobenzoyl group or a 2-(4-chlorobenzamido)ethyl group and R$_o$ represents a hydrogen atom or a branched or unbranched C$_1$–C$_4$ alkyl group.

Particularly well-known members of this family are (i) clofibrate, which has the nomenclature: ethyl ester of 4-chlorophenoxy-2-methylpropanoic acid or ethyl 2-(4-chlorophenoxy)-2-methylpropanoate, and (ii) fenofibrate, which has the nomenclature: 1-methylethyl ester of 2-[4-(4-chlorobenzoyl)phenoxy]-2-methylpropanoic acid or isopropyl 2-[4-(4-chlorobenzoyl)phenoxy]-2-methylpropanoate.

It is known that various methods for the synthesis of fibrates have already been recommended in the past. British Pat. No. GB -A-860 303, which relates to the preparation of clofibrate, proposes the reaction of a phenol of the formula 4-ClC$_6$H$_4$OH with an acetone/chloroform mixture in the presence of sodium hydroxide, followed by esterification of the resulting acid with ethyl alcohol.

British Pat. No. GB -A-1 415 295, which relates to the preparation of fenofibrate, proposes a method analogous to that of the above-mentioned British Pat. No. GB -A-860 303 and comprising the following steps:

(a) reaction of an acetone/chloroform mixture with (4-chlorophenyl)(4-hydroxyphenyl)methanone, (b) conversion of the acid obtained according to the said reaction into the acid chloride, and then (c) esterification of the said acid chloride by reaction with isopropyl alcohol.

Furthermore, British Patent No. GB - A-1 539 897 indicates that it is possible to obtain the compounds of the formula:

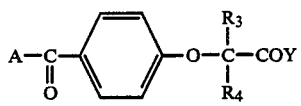   (II)

in which, in particular, A is a phenyl radical substituted by a halogen atom, R$_3$ and R$_4$, which are identical or different, each represent the hydrogen atom or an alkyl group and Y represents a hydroxyl group or an alkoxy group, either by the so-called "acetone/chloroform" method using the said acetone/chloroform mixture, or by condensation of a substituted phenol of the formula:

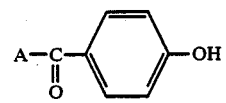   (III)

with a bromine derivative of the formula:

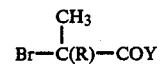   (IV)

in an appropriate solvent.

Depending on the nature of the group R which it is desired to obtain in the final product, especially starting from the 2-bromopropanoic acid derivative of the above formula IV containing the said group R, it is more particularly recommended in British Pat. No. GB - A-1539 897:

(i) not to use the reaction III+IV when R is CH$_3$, but to use the so-called "acetone/chloroform" method in order to obtain a 2-phenoxy-2-methylpropanoic acid derivative belonging to the fibrate group of compounds, and (ii) to use the reaction III+IV when R is H in order to obtain a 2-phenoxypropanoic acid derivative, the said reaction of the phenol III with the bromine derivative IV being carried out in an organic solvent such as ethanol or methyl isobutyl ketone, in the presence of K$_2$CO$_3$.

Thus, according to the description in British Pat. No. GB -A-1 539 897, ethyl 2-[4-(4-chlorobenzoyl)phenoxy]propionate is obtained with a yield fo 76% when ethyl 2-bromopropanoate (i.e. the compound of the formula IV in which R=H and Y=OCH$_2$CH$_3$) is reacted in approximately molar proportions with (4-chlorophenyl)(4-hydroxyphenyl)methanone (i.e. the compound of the formula III in which A is 4-ClC$_6$H$_4$ and which also corresponds to the nomenclature: 4-(4-chlorobenzoyl)(phenol) in methyl isobutyl ketone, in the presence of K$_2$CO$_3$.

Austrian Pat. No. AT -A-367 390 has furthermore disclosed a method for the preparation of 2-(3-phenoxyphenoxy)propanoic acid derivatives, in which the phenyl groups are substituted especially by halogen atoms, by a solventless reaction mechanism. In particular, according to Austrian Pat. No. AT - A-367 390, methYl 2-{[6-chloro-3-(2,4-dichlorophenoxy)]phenoxy}propanoate is prepared by the solventless reaction of 6-chloro-3-(2,4-dichlorophenoxy)phenol with methyl 2-bromopropanoate in the presence of K$_2$CO$_3$. Comparison of the yields of this reaction carried out with a solvent (methanol) [yield: 76%], according to the teaching of British Pat. No. GB - A-1 539 897, or without a solvent [yield: 72%], according to Austrian Pat. No. AT - A-367 390, shows that there are no significant differences between the solvent technique and the solventless technique.

According to the invention, a novel technique is recommended for solving the problem of fibrate synthesis. This technique, which leads to appreciably higher yields than the closest prior art, surprisingly contradicts firstly the teaching of British Pat. No. GB -A-1 539 897 by involving the reaction of a bromine derivative of the formula IV in which R is CH$_3$ with a phenol of the formula III in the absence of a solvent, and secondly the teaching of Austrian Pat. No. AT - A-367 390 by significantly improving the yields.

The method according to the invention for the preparation of a fibrate of the formula:

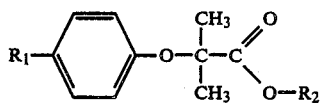

in which $R_1$ represents especially a halogen atom (in particular F, Cl or Br, the preferred halogen being Cl), an acetyl group, a (4-chlorophenyl)hydroxymethyl group of the formula 4-ClC$_6$H$_4$CH(OH), a 4-chlorobenzoyl group or a 2-(4-chlorobenzamido)ethyl group and $R_2$ represents a $C_1$–$C_4$ alkyl group with a linear or branched hydrocarbon chain, comprises reacting an excess, relative to the stoichiometric conditions, of an alkyl 2-bromo-2-methylpropanoate of the formula:

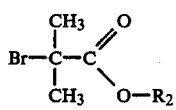

in which $R_2$ is defined as indicated above, with a substituted phenol of the formula:

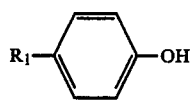

in which $R_1$ is defined as indicated above, in the absence of a solvent and in the presence of an excess of $K_2CO_3$, relative to the stoichiometric conditions, at a temperature greater than or equal to 120° C., for at least 2 hours.

In one embodiment of this method, the resulting fibrate is isolated from the reaction medium directly by precipitation, extraction or distillation.

In another embodiment, the reaction medium containing the fibrate produced by the reaction V+VI is treated with a strong acid (especially HCl or H$_2$SO$_4$) to neutralize the excess $K_2CO_3$, and the fibrate thus obtained is then isolated from the resulting reaction medium by precipitation, extraction or distillation.

The fibrate obtained by the method of the invention is isolated by carrying out one of the following operations: (i) precipitation if the said fibrate is a solid (as in the case of fenofibrate and its analogs of the formula I above), or (ii) extraction with an appropriate solvent or distillation if the said fibrate is liquid or oily (as in the case of clofibrate).

The stoichiometric conditions correspond to the reaction of 1 mol of VI with 1 mol of V in the presence of 0.5 mol of $K_2CO_3$. As indicated above, the reaction VI+V is carried out in such a way that the bromine derivative V and $K_2CO_3$ are in excess relative to the said stoichiometric conditions. Advantageously, 1 mol of substituted phenol of the formula VI will be reacted with about 1.7 to about 2.3 mol of derivative of the formula V in the presence of about 0.8 to about 1.8 mol of $K_2CO_3$, at a temperature of 120° to 160° C., for 3 to 6 hours.

Where appropriate, the neutralization of the excess $K_2CO_3$ with a strong acid is carried out at a temperature not exceeding 120° C. and preferably at a temperature of the order of 100° C. The strong acid is advantageously a mineral acid such as HCl or, preferably, H$_2$SO$_4$.

To summarize, the method according to the invention for the preparation of an ester of the formula I comprises the following two or three steps:

(1) about one mol of VI is reacted with about 1.7 to about 2.3 mol of V (preferably about 2 mol of V), in the absence of a solvent and in the presence of about 0.8 to about 1.8 mol of $K_2CO_3$ (preferably about 1 mol of $K_2CO_3$), at a temperature of 120° C. to 160° C. (preferably at a temperature of 140° C. to 145° C.), for at least 2 hours (preferably for 3 to 6 hours), (2) where appropriate, the excess $K_2CO_3$ is neutralized with a strong acid at a temperature below 120° C., and (3) the fibrate is isolated from the reaction medium by precipitation at a temperature below 60° C., by extraction or by distillation.

The best mode which is recommended for the preparation of fenofibrate by the method according to the invention, consists in:

(a) reacting about 1 mol of VI in which $R_1$ is the 4-chlorobenzoyl group with about 2 mol of V in which $R_2$ is the isopropyl group, in the absence of a solvent and in the presence of about 1 mol of $K_2CO_3$, at a temperature of about 140° C. to about 145° C., for about 5 hours, (b) after the addition of aqueous isopropanol to the resulting reaction medium, neutralizing the excess $K_2CO_3$ with sulfuric acid at a temperature of the order of 100° C., (c) cooling the reaction medium to a temperature of between 15 and 25° C. and collecting the precipitate of fenofibrate by filtration, (d) washing the precipitate of fenofibrate collected in this way with sodium hydroxide and water in succession, and (e) recrystallizing the fenofibrate from aqueous isopropanol.

The method according to the invention is also applicable to the preparation of fibrates which, like bezafibrate, have a carboxylic acid group,$R_o$=H, instead of a carboxylate group. However, in view of the yield of the reaction phenol VI+bromine derivative V in which $R_2$ is H, the operation is preferably carried out in two stages, namely: preparation of the corresponding ester, by the method of the invention, from a bromine derivative V in which $R_2$ is an alkyl group, followed by saponification of the said ester to give the desired acid.

Table I which follows summarizes the results of the comparative experiments which were undertaken to demonstrate the value of the method of the invention (Ex. 1) for the solventless reaction V+VI, relative to the use of the same reaction with a solvent (CP1–CP4), according to the teaching of British Pat. No. GB - A-1 539 897; for the synthesis of fenofibrate. For convenience, Table I also shows the yields of the preparation of fenofibrate by the so-called "acetone/chloroform" method (CP6) and of ethyl 2-[4(4-chlorobenzoyl)-phenoxy](CP5) according to the reaction III+IV in which R is H, in the presence of a solvent. The solvents used in comparative examples CP1 and CP2 are those mentioned specifically in British Pat. No. GB - A-1 539 897 and the solvents used in comparative examples CP3 and CP4 are included in the teaching of British Pat. No.

GB - A-1 539 897, although they are not specifically illustrated by examples in the said document.

The invention will be understood more clearly from the following description of an example of preparation by the method recommended here, and comparative examples according to the closest prior art (British Pat. No. GB - A-1 539 897), for the preparation of fenofibrate, as well as examples for the preparation of other fibrates.

PREPARATION I (Example 1)

Preparation of the 1-methylethyl ester of 2-[4-(4-chlorobenzoyl)phenoxy]-2-methylpropanoic acid (fenofibrate)

465 g (2 mol) of (4-chlorophenyl)(4-hydroxyphenyl)methanone and 815 g (3.9 mol) of the 1-methylethyl ester of 2-bromo-2-methylpropanoic acid (alternative nomenclature: isopropyl 2-bromo-2-methylpropanoate) are introduced into a 4 liter reactor equipped with a stirrer and a condenser. The medium is heated to 120° C. and 265 g (1.92 mol) of potassium carbonate are then added with the aid of a funnel for solids. The reaction medium is subsequently heated for 5 hours at 140°–145° C. and then cooled to about 100° C. It is subsequently diluted with aqueous isopropyl alcohol and then acidified with sulfuric acid. The reaction medium is then cooled to 18°–20° C. in order to crystallize the product, which is filtered off and washed with sodium hydroxide solution and then water. The product is recrystallized from isopropanol to give 605 g of fenofibrate (yield=83.9%) with a purity greater than 99.5% (determination by high pressure liquid chromatography, abbreviated to HPLC).

PREPARATION II (Comparative Example CP 1)

46.5 g 0.2 mol) of (4-chlorophenyl)(4-hydroxyphenyl)methanone, 35 g (0.25 mol) of potassium carbonate and 400 ml of 4-methylpentan-2-one (alternative nomenclature: methyl isobutyl ketone) are introduced into a 1 liter 3-necked round-bottomed flask equipped with a stirrer and a condenser. The mixture is heated under reflux for 2 hours in order to form the potassium salt of (4-chlorophenyl)(4-hydroxyphenyl)methanone, after which 41.8 g (0.2 mol) of the 1-methylethyl ester of 2-bromo-2-methylpropanoic acid are added. The mixture is heated under reflux for 12 hours. After cooling, the insoluble inorganic salts are filtered off and the filtrate is concentrated under reduced pressure. The resulting residue is taken up with ethyl ether and washed with 4% sodium hydroxide solution and then water. After the solvent has been evaporated off, the residue is recrystallized from isopropyl ether to give 20 g of fenofibrate (yield=27.7%).

PREPARATION III (Comparative Example CP 2)

200 ml of anhydrous ethanol are introduced into a 500 ml 3-necked round-bottomed flask equipped with a stirrer and a condenser. 4.6 g (0.2 gram atom) of sodium are then added in portions. When all the sodium has dissolved, 46.5 g (0.2 mol) of (4-chlorophenyl)(4-hydroxyphenyl)methanone are added and the mixture is heated under reflux for 30 minutes. 41.8 g (0.2 mol) of the 1-methylethyl ester of 2-bromo-2-methylpropanoic acid are then added and the mixture is heated under reflux for 8 hours. After concentration, the reaction medium is treated in the same way as in Preparation II. Recrystallization gives 25 g of fenofibrate (yield=34.7%).

PREPARATION IV (Comparative Example CP 3)

1 liter of isopropyl alcohol, 232.5 g (1 mol) of (4-chlorophenyl)(4-hydroxyphenyl)methanone, 138 g (1 mol) of potassium carbonate and 355 g (1.7 mol) of the 1-methylethyl ester of 2-bromo-2-methylpropanoic acid are introduced into a 4 liter reactor equipped with a stirrer and a condenser. The reaction medium is heated gently, with vigorous stirring, and then kept under reflux for 8 hours. About 400 ml of isopropyl alcohol are then distilled off, after which the medium is cooled, with stirring. The precipitate formed is filtered off and then washed with water in the heterogeneous phase, with shaking. It is filtered off and then washed again with 2% sodium hydroxide solution and then with water until the washings are neutral. The product is filtered off and purified by recrystallization from isopropyl alcohol to give 140 g of fenofibrate (yield=38.8%).

PREPARATION V (Comparative Example CP 4)

300 ml of dimethylformamide, 100 g (0.43 mol) of (4-chlorophenyl)(4-hydroxyphenyl)methanone and 68.2 g (0.49 mol) of potassium carbonate are introduced into a 1 liter 3-necked round-bottomed flask. The mixture is heated at the reflux temperature of the solvent for 0.5 h, with vigorous stirring, and 120 g (0.57 mol) of the 1-methylethyl ester of 2-bromo-2-methylpropanoic acid are then added. The mixture is kept under reflux for 4 hours. After cooling, the reaction medium is hydrolyzed with water and then extracted with chloroform. The organic phase is subsequently washed with 3% by weight sodium hydroxide solution and then with water until the washings are neutral. The residue obtained after the solvent has been evaporated off is recrystallized from isopropyl alcohol to give 30 g of fenofibrate (yield=19.3%).

PREPARATION VI (Example 1)

Preparation of the 1-methylethyl ester of 2-[4-(4-chlorobenzoyl)phenoxy]-2-methylpropanoic acid (fenofibrate)

100 g (0.43 mol) of (4-chlorophenyl)(4-hydroxyphenyl)methanone and 165 g (0.79 mol) of the 1-methylethyl ester of 2-bromo-2-methylpropanoic acid are introduced, under a nitrogen atmosphere, into a 3-necked round-bottomed flask equipped with a stirrer and a condenser. The reaction medium is heated to 110° C. and a solution of 50 g (0.36 mol) of potassium carbonate in 50 ml of demineralized water is then added slowly over a period of 20 minutes, with distillation taking place at 100° C. The distillate separates out into 2 phases. The lower phase is recycled into the reaction medium. After heating at 110°–112° C. for 1.5 h, the reaction medium is brought to 140° C. and a temperature of 140°–145° C. is maintained for 4 hours. The reaction medium is then cooled to about 90° C. and 210 ml of 80% isopropyl alcohol are added. The mixture is then left to cool for 12 h, with stirring, after which the suspension obtained is filtered at 0° C. The precipitate is washed with 4 times 200 ml of demineralized water and then recrystallized from propan-2-ol to give 119.5 g (yield=77%) of fenofibrate.

PREPARATION VII (Example 2)

Preparation of 2-{4-[2-(4-chlorobenzoylamino)ethyl]-phenoxy}-2-methylpropanoic acid (bezafibrate)

(1) 27.5 g (0.1 mol) of 4-[N-(4-chlorobenzoyl)-2-aminoethyl]phenol and 38 g (0.18 mol) of the 1-methylethyl ester of 2-bromo-2-methylpropanoic acid are introduced, under a nitrogen atomsphere, into a 500 ml roundbottomed flask equipped with a stirrer and a condenser. The reaction medium is heated to 135° C. and 20 g (0.145 mol) of potassium carbonate are then added slowly. The temperature is raised to 140°-145° C. for 4 h, with stirring. 5 g (0.024 mol) of the 1-methylethyl ester of 2-bromo-2-methylpropanoic acid and 5 g (0.036 mol) of potassium carbonate are then added. The reaction medium is kept at 145° C. for 1 h and then cooled to 100° C. 100 ml of propan-2-ol are added, with vigorous stirring, followed by a mixture of 80 ml of propan-2-ol, 6 ml of sulfuric acid and 30 ml of water. The mixture is left to cool and the precipitate formed is filtered off. 43 g of product are obtained by successively forming a paste with 1% sodium hydroxide solution and then washing with water until the washings are neutral. This product is recrystallized from 90% propan-2-ol to give 36.4 g (yield=90%) of the 1-methylethyl ester of 2-{4-[2-(4-chlorobenzoylamino)ethyl]phenoxy}-2-methylpropanoic acid melting at 84° C.

(2) 36 g the ester obtained above are hydrolyzed with 4.25 g of sodium hydroxide in 130 ml of methanol, at 50° C., for 1 h. After concentration, the residue is taken up with water. The aqueous phase is washed with ether and then acidified in the cold. The expected acid precipitates. The precipitate is filtered off, washed with water and dried to give 26 g (yield=80%) of bezafibrate melting at 183° C.

PREPARATION VIII (Example 3)

Preparation of 2[-4-(2,2-dichlorocyclopropyl)phenoxy]-2-methyl-propanoic acid (ciprofibrate)

(1) 1500 g (11 mol) of methyl-(4-hydroxyphenyl)methanone and 3800 g (18.2 mol) of the 1-methylethyl ester of 2-bromo-2-methylpropanoic acid are introduced into a 6 l reactor under a nitrogen atmosphere. The mixture is heated to 120° C. and 1300 g (9.4 mol) of potassium carbonate are added slowly. A mixture of water and organic products distils off. The temperature is raised to 140° C. After 1 hour, 350 g (1.7 mol) of the 1-methylethyl ester of 2-bromo-2-methylpropanoic acid and then 222 g (1.6 mol) of potassium carbonate are added. The temperature is kept at 140° C. for 1 hour and then lowered to 80° C. 4 liters of propan-2-ol are then added and the mixture is left to cool, with stirring. The insoluble inorganic salts are filtered off and the filtrate is concentrated under reduced pressure. The residue is taken up with ethyl acetate and washed with 10% sodium hydroxide solution and then water. The organic phase is dried and concentrated and the oil obtained is distilled at 136°-138° C. under 0.5 mm of mercury to give 2350 g (yield=81%) of the 1-methylethyl ester of 2-(4-acetylphenoxy)-2-methylpropanoic acid.

(2) 2350 g (8.9 mol) of the ester obtained above and 3 liters of methanol are introduced into a 10 liter reactor under a nitrogen atmosphere. The reaction medium is cooled to 0° C. and 576.5 g (10.68 mol) of potassium borohydride are added slowly, with vigorous stirring. Stirring is maintained for 12 h at room temperature and the mixture is then concentrated under reduced pressure. The residue is treated with iced water and taken up with ethyl acetate. After washing with water, the organic phase is dried and concentrated to give 2355 g yield=99.5%) of the 1-methylethyl ester of 2-[4-(1-hydroxyethyl phenoxy]-2-methylpropanoic acid in the form of a colorless oil.

(3) 240 ml of chloroform, 120 g (0.453 mol) of the ester obtained above and 3 ml of dimethylformamide are introduced into a 1 liter round-bottomed flask under a nitrogen atmosphere. The mixture is cooled to 0° C. and a solution of 18 ml of phosphorus tribromide in 50 ml of chloroform is then introduced, with stirring. The temperature is kept at 0° C. for 1 h. The reaction medium is then stirred at 30° C. for 1 h, after which 84 g of triethylamine are added. The mixture is heated under reflux for 8 h and then cooled and hydrolyzed on ice. It is extracted with chloroform and the mixture is filtered. After the organic phase has been washed with water and then dried, it is concentrated under reduced pressure to give 105 g (yield=93%) of the 1-methylethyl ester of 2-(4-ethenylphenoxy)-2-methylpropanoic acid.

(4) 5 g of the ester obtained above, 12 ml of chloroform and then 0.5 g of benzyltriethylammonium chloride are introduced into a 100 ml round-bottomed flask. 12 g of sodium carbonate are then added dropwise, after which the mixture is heated at 40° C. for 5 h. The reaction medium is subsequently cooled, hydrolyzed and then extracted with chloroform. After washing with water, the organic phase is dried and concentrated under reduced pressure to give 5 g (yield=75%) of the 1-methylethyl ester of 2-[4-(2,2-dichlorocyclopropyl)-phenoxy]-2-methylpropanoic acid in the form of an oil.

(5) 5 g of the ester obtained above, 20 ml of methanol and 0.84 g of sodium hydroxide are introduced into a 100 ml round-bottomed flask. The mixture is heated at 50°-60° C. for 2 h, with stirring and then concentrated under reduced pressure. The solid obtained is taken up with water and the aqueous solution is washed with ether and then acidified to pH 1 with hydrochloric acid. Extraction is carried out with ethyl acetate. The organic phase is washed with water and then dried and concentrated. The oil obtained crystallizes on the addition of cyclohexane. The solid obtained is recrystallized from toluene to give 3.6 g (yield=82%) of ciprofibrate melting at 115° C.

Preparations I-VIII given above to illustrate the invention and the comparative examples show that the method according to the invention affords the following advantages:

(i) very high yields (83.9%) compared with the prior art involving a solvent (19% to 39%);

(ii) products with the very high purity required in the preparation of a drug;

(iii) an energy saving by reducing the reaction times (essentially reducing the heating times);

(iv) solvent use restricted to crystallizations; and (v) a larger operating unit for the same volume of reactor.

The method according to the invention is directly applicable on the industrial scale

TABLE I

| Example | Method (a) (Preparation) | Solvent | Product obtained | Yield (%) |
|---|---|---|---|---|
| Ex. 1 | A (I) | — | fenofibrate | 83.9 |
| CP 1 | B (II) | CH₃COCH₂CH(CH₃)₂ | fenofibrate | 27.7 |
| CP 2 | B (III) | CH₃CH₂OH | fenofibrate | 34.7 |
| CP 3 | B (IV) | CH₃CHOHCH₃ | fenofibrate | 38.8 |
| CP 4 | B (V) | HCON(CH₃)₂ | fenofibrate | 19.3 |
| CP 5 | C | CH₃CH₂OH | (b) | 76 |
| CP 6 | D ("acetone/chloroform") | | fenofibrate | ≈70 (c) |

NOTES
(a) Method:
A: according to the invention by reaction of VI with BrC(CH₃)₂COOCH(CH₃)₂ in the absence of a solvent;
B: according to the teaching of British Patent GB - A-1 539 897 by reaction of VI with BrC(CH₃)₂COOCH(CH₃)₂ in the presence of a solvent;
C: according to the teaching of British Patent GB - A-1 539 897 by reaction of VI with BrCH(CH₃)COOCH₂CH₃ in the presence of a solvent;
D: according to the teaching of British Patent GB - A-1 539 897 by (i) reaction of VI with an acetone/chloroform mixture, then (ii) esterification of the corresponding acid.
(b) Ethyl 2-[4-(4-chlorobenzoyl)phenoxy]propionate
(c) The overall yield of method D is about 70%; more precisely, fenofibric acid is obtained with a yield of 85% (this acid contains 3 to 4% by weight of unreacted phenol VI) and the esterification is then carried out with a yield of 85%.

What is claimed is:

1. A method for the preparation of a substance selected from the group comprising the fibrates corresponding to the general formula:

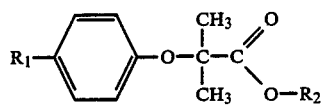

in which $R_1$ represents especially a halogen atom (in particular F, Cl or Br, the preferred halogen atom being Cl) or an acetyl, (4-chlorophenyl)hydroxymethyl, 4-chlorobenzoyl or 2-(4-chlorobenzamido)ethyl group and $R_2$ represents a $C_1$–$C_4$ alkyl group in which the hydrocarbon chain is linear or branched, which comprises reacting an excess, relative to the stoichiometric conditions, of an alkyl 2-bromo-2-methylpropanoate of the formula:

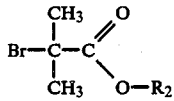

in which $R_2$ is defined as indicated above, with a substituted phenol of the formula:

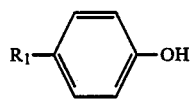

in which $R_1$ is defined as indicated above, in the absence of a solvent and in the presence of an excess of $K_2CO_3$, relative to the stoichiometric conditions, at a temperature greater than or equal to 120° C., for at least 2 h.

2. The method according to claim 1, wherein the resulting fibrate is isolated from the reaction medium by precipitation, extraction or distillation.

3. The method according to claim 1, wherein the reaction medium containing the resulting fibrate is treated with a strong acid to neutralize the excess $K_2CO_3$, and the fibrate is then isolated from the reaction medium by precipitation, extraction or distillation.

4. The method according to claim 1, wherein 1 mol of VI is reacted with about 1.7 to about 2.3 mol of V in the presence of about 0.8 to about 1.8 mol of $K_2CO_3$, at a temperature of 120° to 160° C., for 3 to 6 hours.

5. The method according to claim 1, wherein 1 mol of VI is reacted with about 2 mol of V in the presence of about 1 mol of $K_2CO_3$, at a temperature of 140° to 145° C.

6. The method according to claim 3, wherein the neutralization of the excess $K_2CO_3$ is carried out with sulfuric acid at a temperature not exceeding 120° C. and preferably of the order of 100° C.

7. The method according to claim 1, wherein:
   (1) about one mol of VI is reacted with about 1.7 to about 2.3 mol of V (preferably about 2 mol of V) in the absence of a solvent and in the presence of about 0.8 to about 1.8 mol of $K_2CO_3$ (preferably about 1 mol of $K_2CO_3$, at a temperature of 120° C. to 160° C. (preferably at a temperature of 140° C. to 145° C.), for at least 2 hours (preferably for 3 to 6 hours),
   (2) the excess $K_2CO_3$ is neutralized with a strong acid at a temperature below 120° C., and
   (3) the fibrate is isolated from the reaction medium by precipitation at a temperature below 60° C., or by extraction or distillation.

8. The method according to claim 1 for the preparation of fenofibrate, wherein:
   (a) about 1 mol of VI in which $R_1$ is the 4-chlorobenzoyl group is reacted with about 2 mol of V in which $R_2$ is the isopropyl group, in the absence of a solvent and in the presence of about 1 mol of $K_2CO_3$, at a temperature of about 140° C. to about 145° C., for about 5 hours,
   (b) after the addition of aqueous isopropanol to the resulting reaction medium, the excess $K_2CO_3$ is neutralized with sulfuric acid at a temperature of the order of 100° C.,
   (c) the resulting reaction medium is cooled to a temperature of between 15 and 25° C. and the precipitate of fenofibrate is collected by filtration,
   (d) the precipitate filtered off in this way is washed with sodium hydroxide followed by water, and then
   (e) the fenofibrate is recrystallized from aqueous isopropanol.

9. The method of preparation according to claim 1 for the synthesis of a fibrate of the formula 1 in which $R_2$=H, wherein the corresponding ester is prepared, according to the method of claim 1, by reacting the substituted phenol VI with an alkyl 2-bromo-2-methylpropanoate of the formula V in which $R_2$ is a $C_1$–$C_4$ alkyl group, in the absence of a solvent, and the resulting ester is then saponified.

* * * * *

UNITED STATES PATENT AND TRADEMARK OFFICE

CERTIFICATE EXTENDING PATENT TERM
UNDER 35 U.S.C. § 156

PATENT NO.      :   4,739,101

DATED           :   April 19, 1988

INVENTOR(S)     :   Jean-Pierre Bourgogne et al.

PATENT OWNER    :   Fournier Innovation et Synergie

This is to certify that there has been presented to the

COMMISSIONER OF PATENTS AND TRADEMARKS an application under 35 U.S.C. § 156 for an extension of the patent term. Since it appears that the requirements of the law have been met, this certificate extends the term of the patent for the period of

248 DAYS from the date of expiration of the original patent term, April 27, 2007, with all rights pertaining thereto as provided by 35 U.S.C. § 156(b).

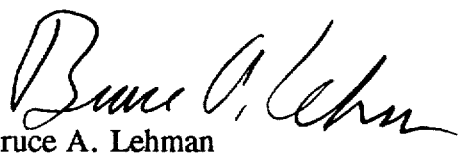

I have caused the seal of the Patent and Trademark Office to be affixed this 23rd day of September 1996.

Bruce A. Lehman
Assistant Secretary of Commerce and
Commissioner of Patents and Trademarks